United States Patent [19]
Wilk

[11] Patent Number: 5,279,542
[45] Date of Patent: Jan. 18, 1994

[54] COLON IRRIGATION METHOD

[76] Inventor: Peter J. Wilk, 185 West End Ave., New York, N.Y. 10023

[21] Appl. No.: 917,597

[22] Filed: Jul. 23, 1992

[51] Int. Cl.⁵ .............................................. A61N 1/30
[52] U.S. Cl. ....................................... 604/19; 604/49
[58] Field of Search ............... 604/19, 21, 22, 24, 604/43, 49, 53, 93, 264; 128/750, 898

[56] References Cited

U.S. PATENT DOCUMENTS

| | | | |
|---|---|---|---|
| 1,652,327 | 12/1927 | Richter | 604/21 |
| 3,527,203 | 9/1970 | Gravlee | 128/150 |
| 3,735,751 | 5/1973 | Katz | 604/24 |
| 4,040,413 | 8/1977 | Ohshiro | 604/21 |
| 4,073,287 | 2/1978 | Bradley et al. | 604/21 |
| 4,551,129 | 11/1985 | Coleman et al. | 604/21 |
| 4,661,094 | 4/1987 | Simpson | 604/53 |
| 4,681,122 | 7/1987 | Winters et al. | 128/784 |
| 4,904,238 | 2/1990 | Williams | 604/264 |
| 4,966,162 | 10/1990 | Wang | 128/150 |
| 4,982,730 | 1/1991 | Lewis, Jr. | 604/22 |

*Primary Examiner*—John D. Yasko
*Assistant Examiner*—Michael Rafa
*Attorney, Agent, or Firm*—R. Neil Sudol; Henry D. Coleman

[57] ABSTRACT

A medical instrument comprises an elongate tube provided essentially along its entire length with a channel and further provided within a distal end region with a plurality of longitudinally and circumferentially spaced apertures communicating with the channel. A pressurized source of irrigation fluid is operative connected to the tube for feeding fluid through the channel and out through the apertures with an essentially uniform radial distribution. The tube is thin enough to fit down the biopsy channel of an endoscope.

2 Claims, 1 Drawing Sheet

COLON IRRIGATION METHOD

BACKGROUND OF THE INVENTION

This invention relates to a medical instrument. This invention relates more particularly to an irrigation instrument for use in laparoscopic and endoscopic surgery. This invention also relates to an associated endoscopic technique, particular for use in cleaning the colon.

In laparoscopic and endoscopic diagnostic investigations and surgery, fiber optic instruments are used to visually inspect internal parts of a patient's anatomy through small incisions or natural openings (mouth, anus) in the patient. Frequently, fluids are needed at the distal end of the laparoscope or endoscope to clean a transparent light receiving surface or to clear a site of blood, faeces or other organic debris to facilitate the transmission of optical radiation.

Generally, irrigation is accomplished in endoscopes and laparoscopes by feeding water or a saline solution through a biopsy channel or an irrigation channel of the instrument. Frequently, this irrigation technique is not particularly effective in attaining the desired end results. Laparoscopic surgeons and endoscopists must adapt themselves to the equipment.

OBJECTS OF THE INVENTION

An object of the present invention is to provide an improved method for providing an irrigating fluid to a distal end of a laparoscope or endoscope or to a surgical site in laparoscopic or endoscopic surgery.

Another object of the present invention is to provide an associated instrument or device for use in such a method.

Other objects of the present invention will be apparent from the detailed descriptions and drawings included herein.

SUMMARY OF THE INVENTION

A medical instrument comprises, in accordance with the present invention, an elongate tube provided essentially along its entire length with a channel and further provided within a distal end region with a plurality of apertures communicating with the channel. The apertures are spaced from one another both longitudinally and circumferentially along the tube. A source of fluid pressure is connected to the tube for feeding a pressurized fluid through the channel and out through the apertures. The apertures are relatively dimensioned so that the fluid is ejected from the distal end of the tube in an essentially uniform radial distribution.

Where the instrument is for use in endoscopic investigations, the tube is flexible and has a diameter smaller than that of a biopsy channel of an endoscope, whereby the tube may be inserted through such biopsy channel. Of course, the tube is longer than the biopsy channel of the endoscope.

Pursuant to another feature of the present invention, the tube is closed at a distal tip, the apertures being located proximally of that tip.

In an endoscopic method in accordance with the present invention, an endoscope having an elongate flexible insertion member with a biopsy channel is provided. Also provided is an elongate flexible tube having a duct extending essentially along its entire length and further having within a distal end region a plurality of apertures communicating with the duct. The endoscopic method also comprises, in accordance with the present invention, the steps of inserting the insertion member into a patient'colon, sliding the tube through the biopsy channel so that the distal end portion of the tube protrudes out a distal end of the biopsy channel, and feeding a pressurized fluid through the duct and out through the aperture thereby cleaning the colon of faeces and/or blood to facilitate, for example, endoscopic surgery on the colon.

Pursuant to another feature of the present invention, the apertures are spaced from one another both longitudinally and circumferentially along the tube, the step of feeding including the step of forcing the fluid out through the apertures simultaneously.

A method for providing an irrigating fluid to a distal end of a laparoscope or endoscope or to a surgical site in laparoscopic or endoscopic surgery, in accordance with the present invention, is more effective than conventional techniques. The irrigating fluid is sprayed out at a plurality of nozzles simultaneously, rather than being ejected from a single aperture at the distal end of the laparoscope or endoscope. The nozzles are distributed through a region in advance of the endoscopic instrument. This distribution enhances irrigation procedures.

An irrigation tube in accordance with the present invention is simple to use and inexpensive to manufacture.

DETAILED DESCRIPTION

Figure 1:
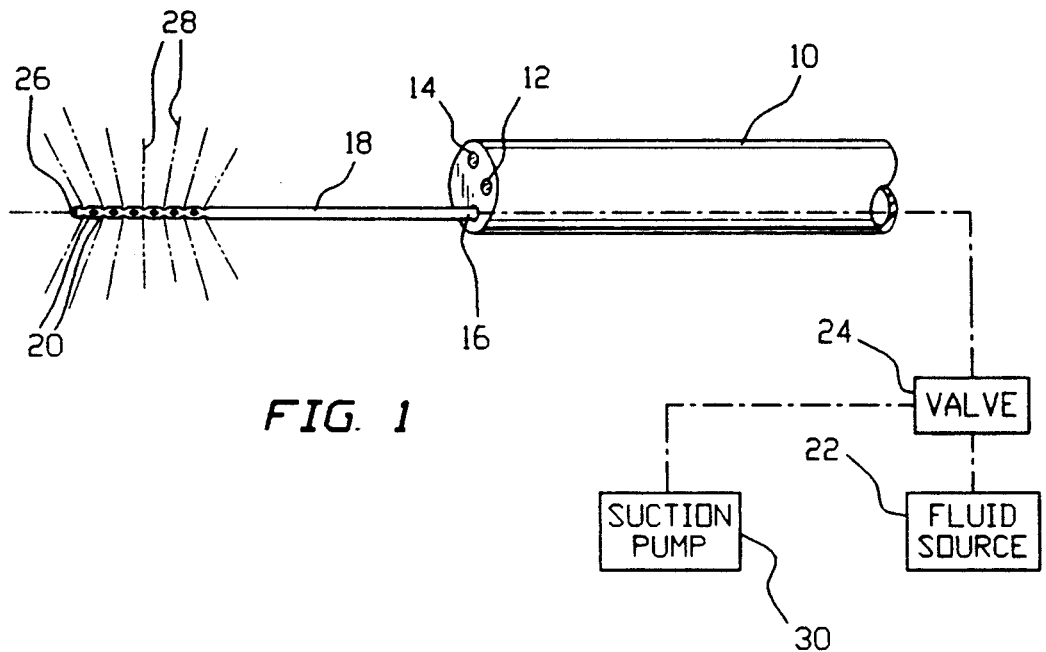
FIG. 1 is a schematic side perspective view of a distal end of an endoscopic insertion member with an irrigation device, in accordance with the present invention.

As illustrated in FIG. 1, an endoscopic insertion member 10 has, at a distal end, a first transparent window or lens 12 for the emission of illuminating radiation, a second transparent window or lens 14 for the reception of radiation reflected from organic surfaces internal to a patient, and a biopsy channel 16. Insertion member 10 may have other conventional components which are not shown in the drawing.

An elongate tube 18 is slidably inserted through biopsy channel 16. Tube 18 is provided essentially along its entire length with a channel or duct (not illustrated) and is further provided within a distal end region with a plurality of apertures 20 communicating with the channel or duct.

At a proximal end of endoscopic insertion member 10, tube 18 is connected to a source 22 of pressurized irrigation fluid. Source 22 selectively communicates with the channel or duct of tube 18, for example, via a manually operable valve member 24, so that the pressurized irrigation fluid may be forced through the duct and ejected or sprayed out through apertures 20. Apertures 20 thus act as respective nozzles or spray outlets. Apertures 20 are spaced from one another both longitudinally and circumferentially along the tube. In addition, apertures 20 are relatively dimensioned so that the irrigation fluid is ejected from the distal end of tube 18 in an essentially uniform radial distribution.

It is to be noted that tube 18 is flexible and has a diameter smaller than that of biopsy channel 16, whereby the tube may be inserted through such biopsy channel. Of course, tube 18 is longer than biopsy channel 16 whereby a distal portion of tube 18 which includes apertures 20 is ejected from endoscope 10 into a patient's colon to clean the colon of faeces, etc.

Tube 18 is optionally closed at a distal tip 26, the apertures being located proximally of that tip. However, inasmuch as an even distribution of jets 28 of irrigation fluid may be desired, an output at distal tip 26 may be included.

Upon an insertion of insertion member 10 into a patient, tube 18 is slid through biopsy channel 16 so that the distal end portion of tube 18 protrudes from the distal end of the biopsy channel, as illustrated in the drawing. Valve member 24 is then actuated to permit the passage of irrigation fluid under pressure along tube 18 to apertures or outlets 20. The irrigation fluid is forced out through all apertures 20 essentially simultaneously.

Valve 24 is also connected to a suction pump 30, whereby the channel or duct of tube 18 may be subjected to a vacuum for purposes of drawing fluidized material in through apertures 20 simultaneously. The arrangement and dimensions of apertures 20 facilitate the evacuation of an irrigated or flooded region inside a patient.

Figure 2:
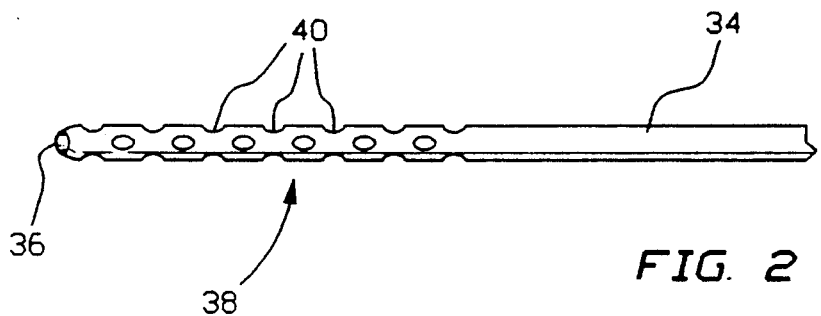
FIG. 2 is a partial schematic side view of a modified irrigation device in accordance with the present invention.

As illustrated in FIG. 2, the distal tip of an irrigation tube 34 is provided with an aperture 36. A distal end portion 38 of the tube 34 is provided with longitudinally and circumferentially equispaced apertures 40 which are dimensioned, together with aperture 36, so that an essentially uniform radial and axial distribution of fluid spray is attained.

Although the invention has been described in terms of particular embodiments and applications, one of ordinary skill in the art, in light of this teaching, can generate additional embodiments and modifications without departing from the spirit of or exceeding the scope of the claimed invention. For example, an irrigation tube in accordance with the present invention may be substantially inflexible if used with a rigid laparoscopic or endoscopic instrument having a biopsy channel. An irrigation device as described and illustrated herein may be inserted by itself through a trocar sleeve or cannula during a laparoscopic operation if the irrigation tube is made with a sufficiently thick wall to support itself. Accordingly, it is to be understood that the drawings and descriptions herein are proffered by way of example to facilitate comprehension of the invention and should not be construed to limit the scope thereof.

What is claimed is:

1. An endoscopic method comprising the steps of:

providing (a) an endoscope having an elongate flexible insertion member with a biopsy channel and (b) an elongate flexible tube provided essentially along its entire length with a duct and further provided within a distal end region with a plurality of apertures communicating with said duct;

inserting said insertion member into a patient's colon;

sliding said tube through said biopsy channel so that said distal end portion protrudes out a distal end of said biopsy channel;

feeding a pressurized fluid to said duct;

ejecting said fluid under pressure out through said apertures in a substantially uniform radial distribution, thereby cleaning a wall of said colon; and directing fluid from said apertures onto a distal end face of said endoscope to thereby clean said distal end face.

2. The method defined in claim 1 wherein said apertures are spaced from one another both longitudinally and circumferentially along said tube, said step of feeding including the step of forcing said fluid out through said apertures simultaneously.

* * * * *